United States Patent

Streeting et al.

Patent Number: 5,491,156
Date of Patent: Feb. 13, 1996

[54] BENZOXAZOLE, BENZOTHIAZOLE AND BENZIMIDAZOLE DERIVATIVES AS FUNGICIDES

[75] Inventors: Ion T. Streeting, late of Wokingham, England, by Jean Streeting, legal representative; Paul A. Worthington, Maidenhead, England

[73] Assignee: Zeneca Limited, London, United Kingdom

[21] Appl. No.: 196,265

[22] PCT Filed: Oct. 12, 1992

[86] PCT No.: PCT/GB92/01860

§ 371 Date: Feb. 16, 1994

§ 102(e) Date: Feb. 16, 1994

[87] PCT Pub. No.: WO93/08180

PCT Pub. Date: Apr. 29, 1993

[30] Foreign Application Priority Data

Oct. 17, 1991 [GB] United Kingdom ............ 9122098

[51] Int. Cl.⁶ .................. C07D 277/68; A01N 43/78
[52] U.S. Cl. ............ 514/367; 514/375; 514/395; 548/170; 548/171; 548/221; 548/306.4
[58] Field of Search ................... 548/170, 171, 548/221, 306.4; 514/367, 375, 395

[56] References Cited

FOREIGN PATENT DOCUMENTS

| | | |
|---|---|---|
| 0256667 | 2/1988 | European Pat. Off. . |
| 0299694 | 1/1989 | European Pat. Off. . |
| 0363818 | 4/1990 | European Pat. Off. . |
| 0378308 | 7/1990 | European Pat. Off. . |
| 0398692 | 11/1990 | European Pat. Off. . |

*Primary Examiner*—Robert Gerstl
*Attorney, Agent, or Firm*—Marian T. Thomson

[57] ABSTRACT

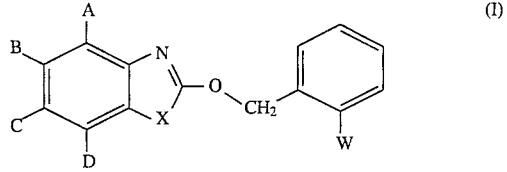

Fungicidal compounds having general formula (I) and stereoisomers thereof, in which A, B, C and D are independently H, halo, $C_{1-4}$ alkyl, $C_{2-4}$ alkenyl, $C_{2-4}$ alkynyl, $C_{1-4}$ alkylthio, cyano, nitro, $C_{1-4}$ haloalkyl, phenoxyobenzyl or benzyloxy, the phenyl moieties of any of the foregoing being optionally substituted with one or more of halo, $C_{1-4}$ alkyl, $C_{1-4}$ alkoxy, nitro or cyano; X is oxygen, sulphur or NR, in which R is H or $C_{1-4}$ alkyl; and W is $CH_3O.CH= C.CO.CH_3$ or $CH_3O.N=C.CONR^1R^2$, in which $R^1$ and $R^2$ are independently H or methyl.

10 Claims, No Drawings

BENZOXAZOLE, BENZOTHIAZOLE AND BENZIMIDAZOLE DERIVATIVES AS FUNGICIDES

This application is A 391 of PCT/GB92/01860 filed Oct. 12, 1992.

This invention relates to benzoxazole, benzothiazole and benzimidazole derivatives useful as fungicides, to processes for preparing them, to fungicidal compositions containing them, and to methods of using them to combat fungi, especially fungal infections of plants.

Certain fungicidal derivatives of benzoxazole, benzothiazole and benzimidazole are described in EP-A-0299694.

According to the present invention there are provided heterocyclic compounds having the general formula (I), and stereoisomers thereof, in which A, B, C and D are independently H, halo (especially fluoro, chloro or bromo), $C_{1-4}$ alkyl (especially methyl or ethyl), $C_{2-4}$ alkenyl, $C_{2-4}$ alkynyl, $C_{1-4}$ alkoxy (especially methoxy or ethoxy), $C_{1-4}$ alkylthio (especially methylthio or ethylthio), cyano, nitro, $C_{1-4}$ haloalkyl (especially trifluoromethyl), phenyl, phenoxy, benzyl or benzyloxy, the phenyl moieties of any of the foregoing being optionally substituted with one or more of halo, $C_{1-4}$ alkyl, $C_{1-4}$ alkoxy, nitro or cyano; X is oxygen, sulphur or NR, in which R is H or $C_{1-4}$ alkyl (especially methyl); and W is $CH_3O.CH\!=\!C.CO_2CH_3$ or $CH_3O.N\!=\!C.CONR^1R^2$, in which $R^1$ and $R^2$ are independently H or methyl.

Because the double bond of the W group is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomer, in which the groups —$OCH_3$ and —$CO_2CH_3$ or $CONR^1R^2$ are on opposite sides of the olefinic bond of the W group, are the more fungicidally active and form a preferred embodiment of the invention.

Of particular interest are the compounds in which W is $CH_3O.Ch\!=\!C.CO_2CH_3$ or $CH_3O.N\!=\!C.CONHCH_3$, especially the (E)-isomers. Also of particular interest are the compounds in which X is sulphur.

Typically A, B, C and D are independently H, halo, $C_{1-4}$ alkyl, $C_{1-4}$ alkoxy, $C_{1-4}$ alkylthio, halo($C_{1-4}$)alkyl, cyano or nitro; and usually each of three of A, B, C and D is 5. More usually one of A and B is H, fluoro, chloro, bromo, methyl, ethyl, methoxy, ethoxy, methylthio, ethylthio, trifluoromethyl, cyano or nitro and the other is H, and each of C and D is H.

In one aspect the invention provides a compound having the general formula (I), especially its (E)-isomer, in which X is sulphur, W is $CH_3O.CH\!=\!C.CO_2CH_3$ and A, B, C and D have the meanings given above. Typically one of A, B, C and D, usually A or B, is halo (especially chloro), $C_{1-4}$ alkyl (especially methyl), $C_{1-4}$ alkoxy (especially methoxy), halo $C_{1-4}$ alkyl (especially trifluoromethyl), cyano or nitro and the others are H.

More particularly the invention provides the (E)-isomers of the compounds in which X is sulphur, W is $CH_3O.CH\!=\!C.CO_2CH_3$, A is H or chloro and B, C and D are all H, i.e. the compounds (E)-methyl 2-[2-(benzothiazol-2-yloxymethyl)phenyl]-3-methoxypropenoate and (E)-methyl 2-[2-(4-chlorobenzothiazol-2-yloxymethyl)phenyl]-3-methoxypropenoate. Table I consists of 87 compounds of formula (I) in which the values of A, B, C, D, W and X are given in the Table.

TABLE I

| Compound No. | A | B | C | D | X | W |
|---|---|---|---|---|---|---|
| 1 | H | H | H | H | S | $CH_3O.CH\!=\!C.CO_2CH_3$ |
| 2 | Cl | H | H | H | S | $CH_3O.CH\!=\!C.CO_2CH_3$ |
| 3 | H | H | H | H | O | $CH_3O.CH\!=\!C.CO_2CH_3$ |
| 4 | H | H | H | H | S | $CH_3O.N\!=\!C.CONHCH_3$ |
| 5 | H | H | H | H | O | $CH_3O.N\!=\!C.CONHCH_3$ |
| 6 | H | Cl | H | H | S | $CH_3O.CH\!=\!C.CO_2CH_3$ |
| 7 | H | H | Cl | H | S | $CH_3O.CH\!=\!C.CO_2CH_3$ |
| 8 | H | H | H | Cl | S | $CH_3O.CH\!=\!C.CO_2CH_3$ |
| 9 | $CH_3$ | H | H | H | S | $CH_3O.CH\!=\!C.CO_2CH_3$ |
| 10 | H | $CH_3$ | H | H | S | $CH_3O.CH\!=\!C.CO_2CH_3$ |
| 11 | $CH_3$ | H | H | H | O | $CH_3O.CH\!=\!C.CO_2CH_3$ |
| 12 | H | $CH_3$ | H | H | O | $CH_3O.CH\!=\!C.CO_2CH_3$ |
| 13 | $CH_3$ | H | H | H | S | $CH_3O.N\!=\!C.CONHCH_3$ |
| 14 | $CH_3O$ | H | H | H | S | $CH_3O.CH\!=\!C.CO_2CH_3$ |
| 15 | H | $CH_3O$ | H | H | S | $CH_3O.CH\!=\!C.CO_2CH_3$ |
| 16 | $CH_3O$ | H | H | H | O | $CH_3O.CH\!=\!C.CO_2CH_3$ |
| 17 | H | $CH_3O$ | H | H | O | $CH_3O.CH\!=\!C.CO_2CH_3$ |
| 18 | $CH_3O$ | H | H | H | S | $CH_3O.N\!=\!C.CONHCH_3$ |
| 19 | H | H | H | H | $NCH_3$ | $CH_3O.CH\!=\!C.CO_2CH_3$ |
| 20 | Cl | H | H | H | S | $CH_3O.N\!=\!C.CONHCH_3$ |
| 21 | H | Cl | H | H | S | $CH_3O.N\!=\!C.CONHCH_3$ |
| 22 | H | H | Cl | H | S | $CH_3O.N\!=\!C.CONHCH_3$ |
| 23 | H | H | H | Cl | S | $CH_3O.N\!=\!C.CONHCH_3$ |
| 24 | F | H | H | H | S | $CH_3O.CH\!=\!C.CO_2CH_3$ |
| 25 | H | F | H | H | S | $CH_3O.CH\!=\!C.CO_2CH_3$ |
| 26 | H | H | F | H | S | $CH_3O.CH\!=\!C.CO_2CH_3$ |
| 27 | H | H | H | F | S | $CH_3O.CH\!=\!C.CO_2CH_3$ |
| 28 | F | H | H | H | S | $CH_3O.N\!=\!C.CONHCH_3$ |
| 29 | H | F | H | H | S | $CH_3O.N\!=\!C.CONHCH_3$ |
| 30 | H | H | F | H | S | $CH_3O.N\!=\!C.CONHCH_3$ |
| 31 | H | H | H | F | S | $CH_3O.N\!=\!C.CONHCH_3$ |
| 32 | Br | H | H | H | S | $CH_3O.CH\!=\!C.CO_2CH_3$ |

TABLE I-continued

| Compound No. | A | B | C | D | X | W |
|---|---|---|---|---|---|---|
| 33 | H | Br | H | H | S | $CH_3O.CH=C.CO_2CH_3$ |
| 34 | H | H | Br | H | S | $CH_3O.CH=C.CO_2CH_3$ |
| 35 | H | H | H | Br | S | $CH_3O.CH=C.CO_2CH_3$ |
| 36 | Br | H | H | H | S | $CH_3O.N=C.CONHCH_3$ |
| 37 | H | Br | H | H | S | $CH_3O.N=C.CONHCH_3$ |
| 38 | H | H | Br | H | S | $CH_3O.N=C.CONHCH_3$ |
| 39 | H | H | H | Br | S | $CH_3O.N=C.CONHCH_3$ |
| 40 | CN | H | H | H | S | $CH_3O.CH=C.CO_2CH_3$ |
| 41 | H | CN | H | H | S | $CH_3O.CH=C.CO_2CH_3$ |
| 42 | H | H | CN | H | S | $CH_3O.CH=C.CO_2CH_3$ |
| 43 | H | H | H | CN | S | $CH_3O.CH=C.CO_2CH_3$ |
| 44 | CN | H | H | H | S | $CH_3O.N=C.CONHCH_3$ |
| 45 | H | CN | H | H | S | $CH_3O.N=C.CONHCH_3$ |
| 46 | H | H | CN | H | S | $CH_3O.N=C.CONHCH_3$ |
| 47 | H | H | H | CN | S | $CH_3O.N=C.CONHCH_3$ |
| 48 | $NO_2$ | H | H | H | S | $CH_3O.CH=C.CO_2CH_3$ |
| 49 | H | $NO_2$ | H | H | S | $CH_3O.CH=C.CO_2CH_3$ |
| 50 | H | H | $NO_2$ | H | S | $CH_3O.CH=C.CO_2CH_3$ |
| 51 | H | H | H | $NO_2$ | S | $CH_3O.CH=C.CO_2CH_3$ |
| 52 | $NO_2$ | H | H | H | S | $CH_3O.N=C.CONHCH_3$ |
| 53 | H | $NO_2$ | H | H | S | $CH_3O.N=C.CONHCH_3$ |
| 54 | H | H | $NO_2$ | H | S | $CH_3O.N=C.CONHCH_3$ |
| 55 | H | H | H | $NO_2$ | S | $CH_3O.N=C.CONHCH_3$ |
| 56 | $CH_3CH_2O$ | H | H | H | S | $CH_3O.CH=C.CO_2CH_3$ |
| 57 | H | $CH_3CH_2O$ | H | H | S | $CH_3O.CH=C.CO_2CH_3$ |
| 58 | H | H | $CH_3CH_2O$ | H | S | $CH_3O.CH=C.CO_2CH_3$ |
| 59 | H | H | H | $CH_3CH_2O$ | S | $CH_3O.CH=C.CO_2CH_3$ |
| 60 | $CH_3CH_2O$ | H | H | H | S | $CH_3O.N=C.CONHCH_3$ |
| 61 | H | $CH_3CH_2O$ | H | H | S | $CH_3O.N=C.CONHCH_3$ |
| 62 | H | H | $CH_3CH_2O$ | H | S | $CH_3O.N=C.CONHCH_3$ |
| 63 | H | H | H | $CH_3CH_2O$ | S | $CH_3O.N=C.CONHCH_3$ |
| 64 | $CH_3S$ | H | H | H | S | $CH_3O.CH=C.CO_2CH_3$ |
| 65 | H | $CH_3S$ | H | H | S | $CH_3O.CH=C.CO_2CH_3$ |
| 66 | H | H | $CH_3S$ | H | S | $CH_3O.CH=C.CO_2CH_3$ |
| 67 | H | H | H | $CH_3S$ | S | $CH_3O.CH=C.CO_2CH_3$ |
| 68 | $CH_3S$ | H | H | H | S | $CH_3O.N=C.CONHCH_3$ |
| 69 | H | $CH_3S$ | H | H | S | $CH_3O.N=C.CONHCH_3$ |
| 70 | H | H | $CH_3S$ | H | S | $CH_3O.N=C.CONHCH_3$ |
| 71 | H | H | H | $CH_3S$ | S | $CH_3O.N=C.CONHCH_3$ |
| 72 | $CH_3CH_2$ | H | H | H | S | $CH_3O.CH=C.CO_2CH_3$ |
| 73 | H | $CH_3CH_2$ | H | H | S | $CH_3O.CH=C.CO_2CH_3$ |
| 74 | H | H | $CH_3CH_2$ | H | S | $CH_3O.CH=C.CO_2CH_3$ |
| 75 | H | H | H | $CH_3CH_2$ | S | $CH_3O.CH=C.CO_2CH_3$ |
| 76 | $CH_3CH_2$ | H | H | H | S | $CH_3O.N=C.CONHCH_3$ |
| 77 | H | $CH_3CH_2$ | H | H | S | $CH_3O.N=C.CONHCH_3$ |
| 78 | H | H | $CH_3CH_2$ | H | S | $CH_3O.N=C.CONHCH_3$ |
| 79 | H | H | H | $CH_3CH_2$ | S | $CH_3O.N=C.CONHCH_3$ |
| 80 | $CF_3$ | H | H | H | S | $CH_3O.CH=C.CO_2CH_3$ |
| 81 | H | $CF_3$ | H | H | S | $CH_3O.CH=C.CO_2CH_3$ |
| 82 | H | H | $CF_3$ | H | S | $CH_3O.CH=C.CO_2CH_3$ |
| 83 | H | H | H | $CF_3$ | S | $CH_3O.CH=C.CO_2CH_3$ |
| 84 | $CF_3$ | H | H | H | S | $CH_3O.N=C.CONHCH_3$ |
| 85 | H | $CF_3$ | H | H | S | $CH_3O.N=C.CONHCH_3$ |
| 86 | H | H | $CF_3$ | H | S | $CH_3O.N=C.CONHCH_3$ |
| 87 | H | H | H | $CF_3$ | S | $CH_3O.N=C.CONHCH_3$ |

TABLE II

Table II gives melting points and selected proton NMR data obtained at 270 MHz for certain compounds described in Table I. Chemical shifts are measured at 20° C. in ppm from tetramethylsilane and deuterochloroform was used as solvent, unless otherwise stated. The following abbreviations are used:

s = singlet  m = multiplet
d = doublet  br = broad
t = triplet  ppm = parts per million

| Compound No | Melting Point (°C.) | Proton NMR Data (δ) |
|---|---|---|
| 1 | 107–108 | 3.69(3H, s); 3.82(3H, s); 5.48(2H, s); 7.16–7.28(2H, m); 7.31–7.44(3H, m); 7.55–7.73(3H, m); 7.59⁺(1H, s) ppm. |
| 2 | 110–112 | 3.69(3H, s); 3.84(3H, s); 5.57(2H, s); 7.07–7.28(2H, m); 7.31–7.45(3H, m); 7.45–7.66(2H, m); 7.58⁺(1H, s) ppm. |
| 4 | 104–105 | 2.92(3H, d); 3.95(3H, s); 5.47(2H, s); 6.76(1H, brs); |

TABLE II-continued

| | | |
|---|---|---|
| | | 7.18–7.29(2H, m); 7.37(1H, t); 7.40–7.51(2H, m); 7.51–7.72(3H, m) ppm. |
| 6 | Oil | 3.70(3H, s); 3.83(3H, s); 5.48(2H, s); 7.11–7.33(2H, m); 7.33–7.43(2H, m); 7.49–7.71(2H, m); 7.59+(1H, s); 7.68(1H, d) ppm. |

+Chemical shift of singlet from olefinic proton on β-methoxypropenoate group (ppm from tetramethylsilane).

The compounds of the invention of formula (I) can be prepared by the steps illustrated in Schemes 1 to 4. Throughout the Schemes the variables A, B, C, D, W and X have the values given above, Y is $HO.CH{=}C.CO_2CH_3$ or $HO.N{=}C.CONR^1R^2$, Z is $CH_2CO_2CH_3$ or $CH_2.CONR^1R^2$, Q is $CO.CO_2CH_3$ or $CO.CONR^1R^2$, Ph is phenyl and L is a leaving group such as halo or $CH_3SO_2.O$.

In Scheme 1, compounds of the invention of formula (I) can be prepared by coupling hydroxy compounds of formula (II) with benzyl compounds of formula (III) in the presence of a base (such as silver carbonate), in a convenient solvent (such as toluene) at a temperature of 20°–110° C.

In an alternative approach, shown in Scheme 2, compounds of the invention of formula (I) can be prepared by coupling benzyl alcohols of formula (V) with compounds of formula (IV) in the presence of a base (such as sodium hydride, sodium carbonate or silver carbonate), in a convenient solvent (such as toluene or N,N dimethylformamide) at a temperature of 20°–110° C.

In Scheme 3, compounds of the invention of formula (I) can be prepared by methylation of the compounds of formula (VI) with a compound $CH_3L$ in the presence of a convenient base (such as sodium hydride or potassium carbonate). The compounds of formula (VI) can be conveniently prepared from the substituted phenylacetic acid derivatives (VII) by methods known in the literature (see, for example, EP-A-0178826, EP-A-0254426, EP-A-0278595, EP-A-0299694 and EP-A-0398692).

In a further alternative approach, shown in Scheme 4, compounds of the invention of formula (I) can be prepared from substituted phenylglyoxylic acid derivatives (VIII) by treatment with the appropriate reagent. For example, when W is $CH_3O.CH{=}C.CO_2CH_3$ compounds of formula (I) can be prepared by treating the derivative (VIII) with the Wittig reagent $Ph_3P{=}CH.OCH_3$ and when W is $CH_3O.N{=}C.CONR^1R^2$ compounds of formula (I) can be prepared by reacting the derivative (VIII) with a substituted hydroxylamine $H_2N.OCH_3$. The intermediate compounds (VII) and (VIII) can be prepared by the same coupling reactions as those described in Schemes 1 and 2.

The compounds of formula (I) in which W is $CH_3O.N{=}C.CONR^1R^2$ can also be prepared from the corresponding compounds (I) in which W is $CH_3O.N{=}C.CO_2H$ by methods set out in the literature and in other ways as described in EP-A-0398692.

In a further aspect, the present invention provides processes for preparing compounds of formula (I).

The compounds are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personarum* on peanuts and other Cercospora species on other hosts, for example, sugar beet, bananas, soya beans and rice; *Botrytis cinerea* (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and Baize; Ramularia spp. on sugar beet and other hosts; post-harvest diseases particularly of fruit (e.g. *Pencillium digitalum* and *P. italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopezicula tracheiphila* and *Stereum hirsutum*; other pathogens on lumber, notably *Cephaloascus fragrans*, Ceratocystis spp., *Ophiostoma piceae*, Penicillium spp., *Trichoderma pseudokoningii, Triehoderma viride Trichoderma harzianum, Aspergillus niger, Leptographium lind-

*beryl* and *Aureobasidium pullulans*; and fungal vectors of vital diseases e.g. *Polymyxa graminis* on cereals as the vector of barley yellow mosaic virus (BYMV).

Some of the compositions show a broad range of activities against fungi in vitro.

Further, some of the compositions may be active as seed dressings against pathogens including Fusarium spp., Septoria spp., Tillella spp., (e.g. bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied the foliage of plants, the compounds of the invention are applied at rates of 0.1 g to 10 kg, preferably 1 g to 8kg, more preferably 10 g to 4kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonire, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

An additional fungicidal compound may be present in the composition of the invention. By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (±)-cis-1-(4--chlorophenyl)-2-(1H-1,2,4-triazol-1-yl)cycloheptanol, (2RS, 3RS)-1-[3-(2-chlorophenyl)-2-(4-fluorophenyl)oxiran-2-ylmethyl]-1H-1,2,4-triazole, (RS)-1-aminopropylphosphonic acid, (RS)-4-(4-chlorophenyl)-2-phenyl-2-(1H-1,2,4-triazol-1-ylmethyl)butyronitrile, (Z)-N-but-2-enyloxymethyl-2-chloro-2',6'-diethylacetanilide, 1-(2-cyano-2--methoxyiminoacetyl)-3-ethyl urea, 3-(2,4-dichlorophenyl)-2-(1H-1,2,4-tri-azol-1-yl)quinazolin-4(3H)-one, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxolacetamido]-γ-butyrolactone, N-(2-methoxy-5-pyridyl)-cyclopropane carboxamide, (E)-methyl 2-[2-(6-(cyanophenoxy)pyrimidin-4-yloxy)phenyl]-3-methoxypropenoate, alanycarb, aldimorph, ampropylfos, anilazine, azaconazole, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, didecyl dimethyl ammonium chloride, diethofencarb, difenoconazole, O,O-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N_-benzyl-N-([methyl(methyl-thioethylideneamino-oxycarbonyl)amino] thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fluoroimide, flutolanil, flutriafol, flusilazole, folpet, fuberidazole, furalaxyl, furconazole-cis, guazatine, hexaconazole, hydroxyisoxazole, hymexazole, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, methfuroxam, metiram, metiram-zinc, metsulfovax, myclobutanil, neoasozin, nickel dimethyldithiocarbamate, nitrothal-iso-propyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyroquilon, pyroxy#ur, pyrrolnitrin, quaternary ammonium compounds, quinconazole, quinomethionate, quintozene, rabenazole, sodium pentachlorophenate, streptomycin, sulphur, tebuconazole, techlofthalam, tecnazene, tetraconazole, thiabendazole, thicarbanil, thicyofen, 2-(thiocyanomethylthio)benzothiazole, thiophanate-methyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, tri#orine, triflumizole, triticonazole, validamycin A, vapam, vinclozolin, zineb and ziram. The compounds of general formula (I) can be mixed with soil, peat or other rooting media for the protection of plants against seed-borne, soil-borne or foliar fungal diseases.

The following Examples illustrate the invention. Throughout the Examples, the term 'ether' refers to diethyl ether, magnesium sulphate was used to dry solutions, and .solutions were concentrated under reduced pressure. Reactions involving air or water sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1$H NMR spectra were recorded using $CDCl_3$- solutions unless otherwise stated. The following abbreviations are use throughout:

| NMR = nuclear magnetic resonance | m = multiplet |
|---|---|
| IR = infrared | br = broad |
| S = singlet | m.p. = melting point |
| d = doublet | ppm = parts per million |
| t = triplet | |

EXAMPLE 1

This Example illustrates the preparation of (E)-methyl 2-[2-(benzo-thiazol-2-yloxymethyl)phenyl]-3-methoxypropenoate (Compound 1 of Table I).

2-Hydroxybenzothiazole (1.56 g) and silver carbonate (2.91 g) were added to a solution of (E)-methyl 2-[2-(bromomethyl)phenyl]-3-methoxypropenoate (2.00 g) in dry toluene (40 ml). The mixture was heated and stirred at 110° C. under a nitrogen atmosphere in the dark. After two hours, more (E)-methyl 2-[2-(bromomethyl)phenyl]-3-methoxypropenoate (1.00 g) was added to the cooled mixture and heating continued for a further four hours. The cooled mixture was diluted with toluene (30 ml), filtered through Hyflo Supercel filter aid and the filtrate concentrated under reduced pressure. The residue was dissolved in dichloromethane (40 ml) and washed with 2N sodium hydroxide solution (2 ×30 ml) and water (25 ml). The dichloromethane solution was dried and concentrated under reduced pressure. Chromatography of the residue on silica gel (Merck 60) using ethyl acetate-n-hexane 1:3 as eluent afforded the title compound as a colourles oil (0.71 g) which crystallised on standing. Recrystallisation from ether-n-hexane yielded a white powder (0.57 g, 15.3%), m.p. 107°–108° C.; IR maxima (nujol mull): 1710, 1630 cm$^{-1}$; $^1$H NMR (CDCl$_3$, 270 MHz): δ3.69(3H,s), 3.82(3H,s) 5.48(2H,s), 7.16–7.28(2H,m), 7.31–7.44(3H,m), 7.55–7.73(3H,m), 7.59(1H,s) ppm.

EXAMPLE 2

This Example illustrates the preparation of (E)-methyl 2-[2-(4-chlorobenzothiazol-2-yloxymethyl)phenyl]-3-methoxypropenoate (Compound 2 of Table I).

(E)-methyl 2-[2-(bromomethyl)phenyl]-3-methoxypropenoate (2.00 g) was treated with 4-chloro-2-hydroxybenzothiazole (1.95 g) and silver carbonate (2.91 g) in dry toluene (45 ml) as described in Example 1. The crude product, obtained after work up as a brown oil (4.37 g), was chromatographed on silica gel (Merck 60) using ethyl acetate-N-hexane 1:2, and then acetone-n-hexane 1:6.5, to afford the title compound as a pale yellow gum (0.30 g) which crystallised on trituration with ether-N-hexane to yield a light yellow powder (0.14 g, 5.1%) m.p. 110°–112° C.; IR maxima (nujol mull): 1705, 1630 cm$^{-1}$; $^1$H NMR (CDCl$_3$, 270 MHz):δ3.69(3H,s), 3.84(3H,s), 5.57(2H,s), 7.07–7.28(2H,m), 7.31–7.45(3H,m), 7.45–7.66(2H,m), 7.58(1H,s) ppm.

EXAMPLE 3

This Example illustrates the preparation of (E)- N-methyl-O-methyl-2-[2-(benzothiazol-2-yloxymethyl)phenyl]oximinoacetamide (Compound 4 of Table I).
Step 1

2-Hydroxybenzothiazole (0.5 g) and silver carbonate (0.91 g) were added to a solution of (E)-methyl O-methyl-2-[2-(bromomethyl)phenyl]oximinoacetate (2.10 g, prepared as described in EP-A-0363818) in dry toluene (25 ml). The mixture was heated and stirred at 110° C. under a nitrogen atmosphere in the dark. After six hours, more 2-hydroxybenzothiazole (0.25 g) and silver carbonate (0.45 g) were added to the cooled mixture and heating continued for a further six hours. The cooled reaction mixture was filtered through Hyflo Supercel filter aid and the liltrate concentrated under reduced pressure. The brown oil (2.53 g) was purified by flash column chromatography on silica gel (Merck 60) using ethyl acetate:n-hexane 2:7 to give (E)-methyl O-methyl-2-[2-(benzothiazol-2-yloxymethyl)phenyl]oximinoacetate (0.16 g, 20%) as a white powder, m.p. 93°–4° C.; $^1$H NMR (CDCl$_3$, 270 MHz): δ3.97(3H,s), 4.04(3H,s), 5.45(2H,s), 7.18–7.29(2H,m), 7.36(1H,t), 7.40–7.54(2H,m), 7.58–7.74(3H,m) ppm; IR maxima (nujol mull): 1735 cm$^{-1}$.
Step 2

Methylamine gas was passed through a suspension of (E)-methyl O-methyl-2-[2-benzothiazol-2-yloxymethyl)phenyl]oximinoacetate (0.119 g) in methanol, with stirring, for 15 minutes. The resulting clear solution was allowed to stand at room temperature for 0.5 hours. Removal of the methanol gave a white crystalline solid which on recrystallisation from n-hexane/diethyl ether gave the title compound (0.100 g, 84%) as a white crystalline solid, m.p. 104°–5° C.; $^1$H NMR (CDCl$_3$, 270 MHz): δ2.92(3H,d), 3.95(3H,s), 5.47(2H,s), 6.76(1H,brs), 7.18–7.29(2H,m), 7.37(1H,t), 7.40–7.51(2H,m), 7.51–7.72(3H,m) ppm; IR maxima (nujol mull): 1665 , 3330 cm$^{-1}$.

EXAMPLE 4

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. Tween 20 was added to give a final concentration of 0.05% when the sprays were applied to cereals.

For most of the tests the compounds were applied to the soil (roots) or to the foliage (by spraying) one or two days before the plant was inoculated with the disease. An exception was the test on Erysiphe graminis in which the plants were inoculated 24 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

| 0 = 0% disease present | 20 = 10.1–20% disease present |
|---|---|
| 1 = 0.1–1% disease present | 30 = 20.1–30% disease present |
| 3 = 1.1–3% disease present | 60 = 30.1–60% disease present |

-continued

5 = 3.1–5% disease present  90 = 60.1–100% disease present
10 = 5.1–10% disease present Each assessment was then expressed as a percentage of the level of disease present on the untreated control plants. This calculated value is referred to as a POCO (Percentage of Control) value. An example of a typical calculation is as follows:

Disease level on untreated control = 90

Disese level on treated plant = 30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table III.

TABLE III

| Compound No of Table I | Pr | Egt | Sn | Po | Tc | Vi | Pv | Pil |
|---|---|---|---|---|---|---|---|---|
| 1 | 90[a] | 0[a] | 10[a] | 0[a] | 30[a] | 0[a] | 0[a] | 3[a] |
| 2 | 0* | 0 | 0 | 0 | 0 | 0 | 0 | 0 |
| 4 | 90 | 0 | 30 | 0 | 0 | 90 | 0 | 0 |
| 6 | 5[a] | 0[a] | 0[a] | 0[a] | 0[a] | 0[a] | 0[a] | 0[a] |

| Key to Diseases | | | |
|---|---|---|---|
| Pr | Puccinia recondita | Tc | Thanetophorus cucumeris |
| Egt | Erysiphe graminis tritici | Vi | Venturia inaegualis |
| Sn | Septoria nodorum | Pv | Plasmopara viticola |
| Po | Pyricularia oryzae | Pil | Phytophthora infestans lycopersici |

CHEMICAL FORMULAE
(in description)

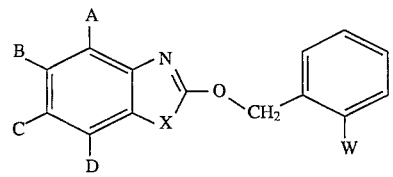

(I)

Scheme 1

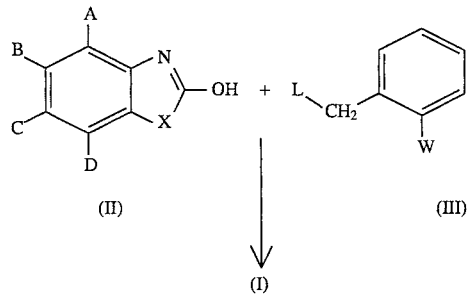

Scheme 2

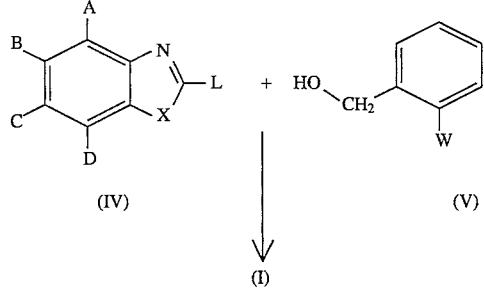

-continued
CHEMICAL FORMULAE
(in description)

Scheme 3

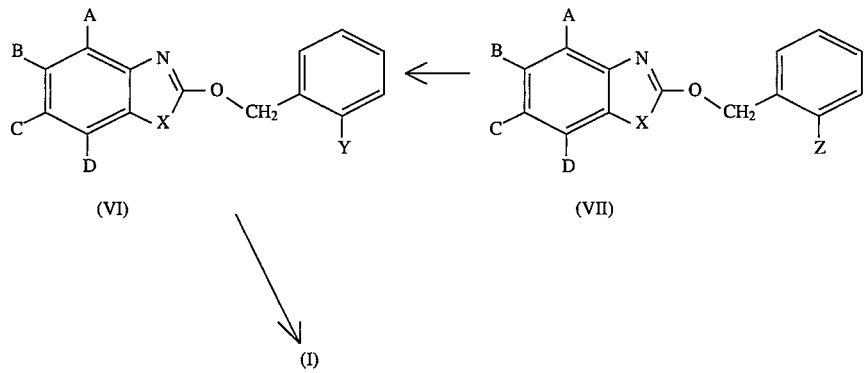

(VI) → (I) ← (VII)

Scheme 4

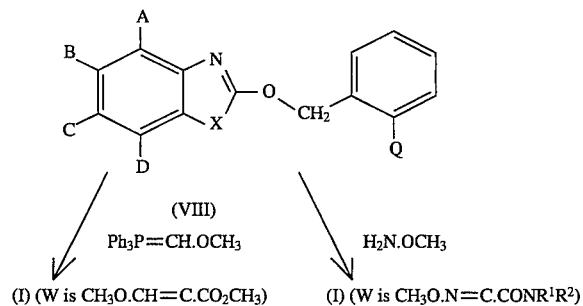

(VIII)

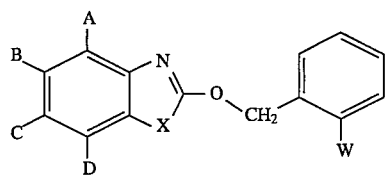

(I) (W is $CH_3O.CH=C.CO_2CH_3$)     (I) (W is $CH_3O.N=C.CONR^1R^2$)

We claim:

1. A compound having the general formula (I):

(I)

and stereoisomers thereof, in which A, B, C and D are independently H, halo, $C_{1-4}$ alkyl, $C_{2-4}$ alkenyl, $C_{2-4}$ alkynyl, $C_{1-4}$ alkoxy, $C_{1-4}$ alkylthio, cyano, nitro, $C_{1-4}$ haloalkyl, phenyl, phenoxy, benzyl or benzyloxy, the phenyl moieties of any of the foregoing being optionally substituted with one or more of halo, $C_{1-4}$ alkyl, $C_{1-4}$ alkoxy, nitro or cyano; X is oxygen, sulphur or NR, in which R is H or $C_{1-4}$ alkyl; and W is $CH_3CH=C.CO_2CH_3$ or $CH_3O.N=C.CONR^1R^2$, in which $R^1$ and $R^2$ are independently H or methyl.

2. A compound according to claim 1 in which W is $CH_3O.CH=C.CO_2CH_3$ or $CH_3O.N=C.CONHCH_3$.

3. The (E)-isomer of a compound according to claim 1.

4. A compound according to claim 1 in which X is sulphur.

5. A compound according to claim 1 in which A, B, C and D are independently H, halo, $C_{1-4}$ alkyl, $C_{1-4}$ alkoxy, $C_{1-4}$ alkylthio, halo($C_{1-4}$)alkyl, cyano or nitro.

6. A compound according to claim 5 in which each of three of A, B, C and D is H.

7. A compound according to claim 1 in which one of A and B is H, fluoro, chloro, bromo, methyl, ethyl, methoxy, ethoxy, methylthio, ethylthio, trifluoromethyl, cyano or nitro, and the other is H, and each of C and D is H.

8. A fungitidal composition comprising a fungicidally effective amount of a compound according to claim 1 and a fungicidally acceptable carrier or diluent therefor.

9. A method of combating fungi which comprises applying to plants, to the seeds of plants or to the locus of the plants or seeds, a fungicidally effective amount of a compound according to claim 1.

10. A method of combatting fungi which comprises applying to plants, to the seeds of plants or to the locus of the plants or seeds, a composition according to claim 8.

* * * * *